United States Patent [19]
Lex

[11] Patent Number: 5,596,412
[45] Date of Patent: Jan. 21, 1997

[54] PROCESS AND DEVICE FOR THE QUANTIFIED ASSESSMENT OF THE PHYSIOLOGICAL IMPRESSION OF REFLECTIVE SURFACES

[75] Inventor: Konrad Lex, Königsdorf, Germany

[73] Assignee: BYK-Gardner, Geretsried, Germany

[21] Appl. No.: 193,209

[22] PCT Filed: Jul. 17, 1992

[86] PCT No.: PCT/EP92/01635

§ 371 Date: Aug. 19, 1994

§ 102(e) Date: Aug. 19, 1994

[87] PCT Pub. No.: WO93/04338

PCT Pub. Date: Mar. 4, 1993

[30] Foreign Application Priority Data

Aug. 16, 1991 [DE] Germany .................. 41 27 215.3

[51] Int. Cl.$^6$ .................................................. G01B 11/30
[52] U.S. Cl. ................................................ 356/371; 356/445
[58] Field of Search ...................................... 356/371, 445, 356/446, 429

[56] References Cited

U.S. PATENT DOCUMENTS

| | | | |
|---|---|---|---|
| 2,812,373 | 5/1974 | Hosoe et al. | 250/562 |
| 3,922,093 | 11/1975 | Dandliker | 356/120 |
| 4,572,672 | 2/1986 | Orchard | 356/446 |
| 4,764,016 | 8/1988 | Johansson | 356/371 |
| 4,966,455 | 10/1990 | Avni et al. | 356/446 |
| 4,977,522 | 12/1990 | David | 364/526 |
| 5,092,676 | 3/1992 | Harata et al. | 356/371 |

FOREIGN PATENT DOCUMENTS 2946493  11/1979  Germany .
9004166  4/1990  WIPO .

Primary Examiner—Richard A. Rosenberger
Attorney, Agent, or Firm—Leydig, Voit & Mayer

[57] ABSTRACT

A process and device for the quantifiable assessment of the physiological impression of reflective surfaces using a point source of light, whose light reflected by the measured surfaces is captured by a photodetector. A series of measured surface values are derived from these measured brightness values for a number of measuring points, which have an exactly defined separation, for which a number of preceding and following measured brightness values are each taken into consideration. The wavelength of the surface disturbances can thereby be determined and analyzed. At least one quality index is derived from the determined measured surface values for the evaluation of the respective surface. The device can be constructed as a hand-held device and moved manually over the surface being tested. For this purpose, the device has at least one measuring wheel, which is rotated by the contact with the surface and whose rotational movement is used to determine the individual measuring points.

10 Claims, 3 Drawing Sheets

PROCESS AND DEVICE FOR THE QUANTIFIED ASSESSMENT OF THE PHYSIOLOGICAL IMPRESSION OF REFLECTIVE SURFACES

BACKGROUND OF THE INVENTION

The invention presented here involves a device and a process for the quantified assessment of the physiological impression of reflective surfaces and particularly of painted surfaces.

For numerous technical products, the quality of the visible surfaces is a critical characteristic for the overall impression of the product. The technical problems which thereby arise are hereafter clarified using the construction of surfaces of motor vehicle bodies which by no means, however, should be understood as a restriction for the application of the invention presented here.

Motor vehicles are usually given a high-gloss paint whose gloss value as a rule far exceeds the gloss value of other surfaces, e.g., furniture surfaces and the like. The high gloss of the paint used and the relatively large surfaces require an exceptionally careful preparation of the areas being painted and a very careful application of the paint. In order to recognize deficiencies in the quality of painted body surfaces, automobile manufacturers today engage a large number of testers who visually test the quality of the surfaces. However, this method involves several disadvantages.

The job of the testers is very demanding and requires work areas whose light conditions are always exactly defined. However, large differences in the evaluation of the same painted surfaces by different testers have been observed, since on the one hand the respective physiological impression is different from tester to tester and since on the other hand the visual faculty of the individual tester is also dependent on his respective physical condition. There are thus great difficulties in defining a lower quality limit which can no longer be accepted without deficiencies and which requires a new painting of the vehicle body. In addition, it is also difficult on the part of experienced testers to determine the causes for unevenness in the paint, so that it is difficult to change the control values of an automatic painting device for improving the quality, based on the observations thus made.

DE-OS 2,946,493 describes a process for assessing the evenness of optically reflecting surfaces. In this process, the surface being tested is illuminated with a point source of light (in the example a 100 Watt halogen lamp and a perforated screen) at a defined distance (in the example 1 m). The light beam which is reflected by the surface being tested is rendered visible on a focusing screen, whereby the brightness distribution of the reflected light depends on the surface structure. In order to determine the brightness distribution, the surface being tested is moved with respect to the lamp and the reflected light is recorded by means of a stationary photodetector. In the example, this photodetector is set up 25 cm from the surface being tested. The variations in brightness then serve as a measurement for evaluating the quality of the surface. The detailed presentation in DE-OS 2,946,493 is referred to concerning the additional state of the art.

The process described above has not been feasible in practice. The reason can be seen primarily in the fact that although a quality index is determined for the quality of the surface, this quality index is not sufficient for characterizing the physiological impression applicable to the evaluation of the surface being tested.

The problem of the invention presented here is, therefore, to further develop a process and a device of the type mentioned above that yields a reproducible, quantified assessment of the physiological impression of reflective surfaces.

An additional aspect of the problem is to create a device which is small and easily constructed and which is designed in such a manner that it can be used by one operator without additional auxiliary devices for the quantified assessment of a surface.

SUMMARY OF THE INVENTION

According to the invention, this problem is solved by a process and the apparatus defined in the claims. The improved apparatus is particularly suitable as a hand-held measuring device.

The preferred embodiments of the invention are the topics of the dependent claims.

The process according to the invention creates the possibility of quantifying the physiological impression of a surface in a reproducible and exact manner. The selected measuring process avoids the inclusion of microscopic properties of the surface, which do not detract from the physiological impression, in the assessment of the quality.

Another particular advantage is the fact that the novel process makes possible an exact analysis of the wavelength of the individual disturbances so that inferences can be made as to the cause of the deficiency in quality.

According to a preferred process, a large number of measured values are first recorded and are evaluated in a process according to the invention. These recorded measured values are designated as measured brightness values. In the subsequent evaluation step, measured surface values, in which a number $N_1$ of preceding measured values and a number $N_2$ of following measured values are each taken into consideration, are derived from the measured brightness values. In this process, the number $N_1$ is preferably equal to the number of $N_2$ measured values. It is obvious that the determination of the measured surface values according to the process assumes that first a number $N_1$ of measured brightness values is recorded before the first determinable measured surface value, and that an additional number $N_2$ of measured brightness values must be recorded after the last measured surface value. Stated simply, the measurement thus requires a preceding run and a following run.

When all measured brightness values have been recorded, the evaluation can also proceed successively with different numbers for $N_1$ and $N_2$. The measurement can thus be evaluated with 50, 40, 30, 20, and 10 preceding and following measuring points (assuming that $N_1$ is selected equal to $N_2$). The long-wave surface disturbances are thus detected better with the higher number of measured values and the short-wave surface disturbances with the lower number.

As the embodiment described below demonstrates, the device can be made very small and compact so that it can be used directly as a hand-held measuring device. In this case, rubber wheels or rubber-covered rolls are preferably used which directly determine the relative movement between surface and device and thus ensure the exact geometric relationship of the measuring points to the since.

BRIEF DESCRIPTION OF THE DRAWINGS

Additional advantages, characteristics, and possibilities for applying the invention presented here are indicated in the following description in conjunction with the drawings in which.

DETAILED DESCRIPTION OF THE PREFERRED EMBODIMENTS

Figure 1:
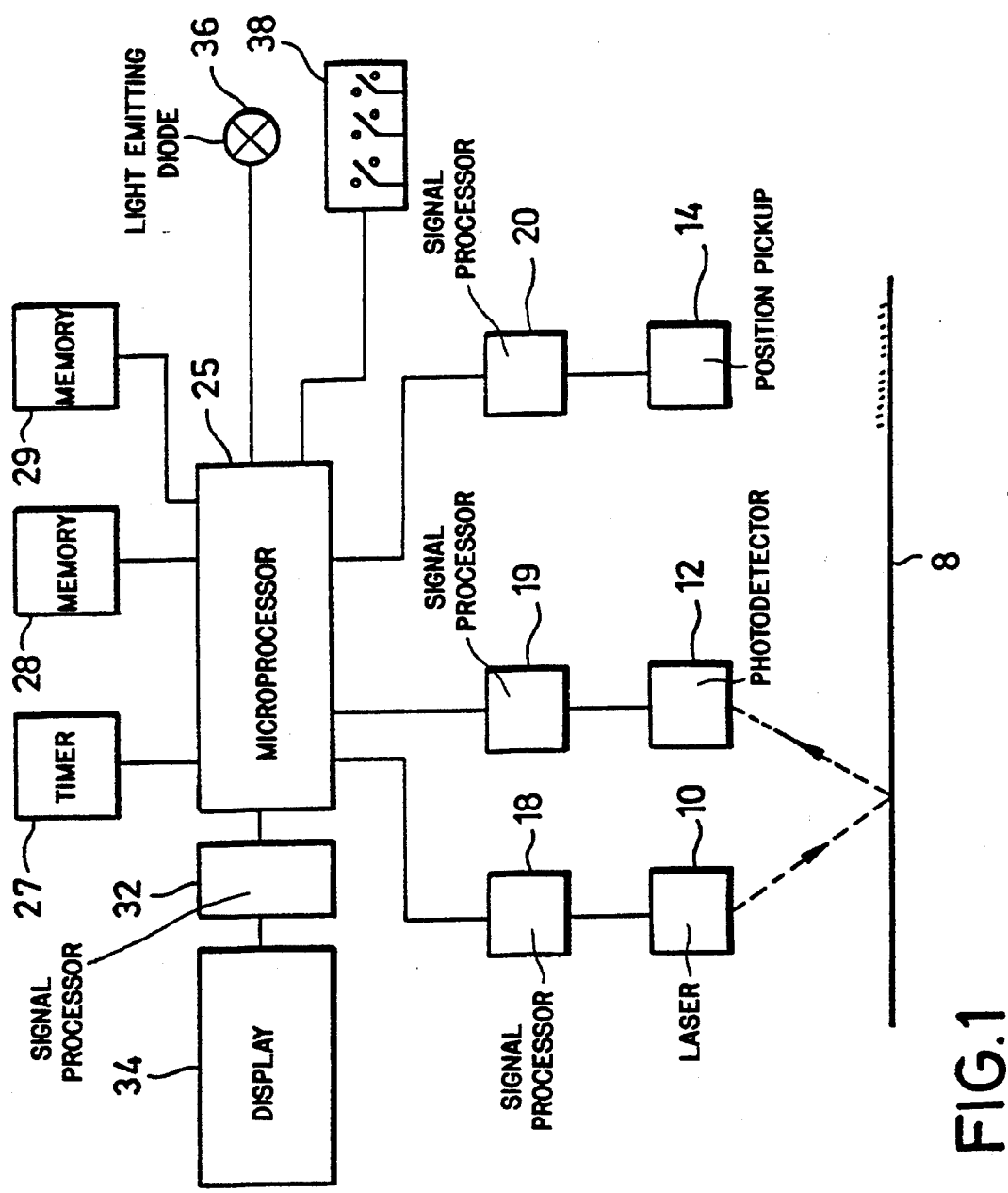
FIG. 1 is a block diagram which describes a process according to the invention and a device according to the invention.
Figure 2A:
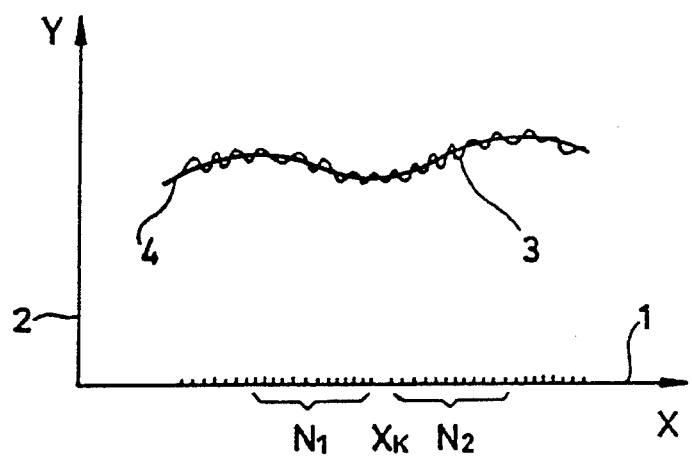
FIG. 2a is a schematic representation for clarifying the recording of the measured values according to the process according to the invention.

The measurement process is first clarified with reference to FIGS. 1 and 2a. FIG. 2a depicts a rectangular coordinate system in which the X-axis 1 corresponds to the surface being measured, and the recorded measured brightness values and the measured surface values obtained by the process according to the invention, from which the quality index is then derived, are plotted on the Y-axis 2. The signal curve of the measured brightness values is indicated with the reference number 3 and the smoothed measured surface values, which are used for the derivation of the quality index, are indicated with the reference number 4.

The measurement of a certain point $X_K$ proceeds as follows.

A number $N_1$ of measured values is first recorded, whose X-coordinate is smaller than $X_K$ and which each have a constant spacing. The X-axis thus directly reproduces the distance coordinate of the surface being measured. After $N_1$ equidistant measured values have been recorded, the actual measured value $X_K$ is recorded and then finally $N_2$ measured values which, in turn, are determined at equidistant straight-line points is measured. In the embodiment presented here, the straight-line spacing of the individual points recorded before the measured value $X_K$ and the spacing of the points recorded after the measured value $X_K$ are equal. Furthermore, the number $N_1$ preceding the measured surface value being recorded is also exactly as great as the number $N_2$ following this value.

The measured surface value for the location $X_K$ is now determined from the recorded measured values $N_1$, $X_K$ and $N_2$. This is done by a statistical analysis of the recorded measured brightness values, e.g., a mean value derivation. Weighing the measured values has proven to be particularly favorable; i.e., allowing the values to enter into the statistical analysis in proportion to their proximity to the measuring point $X_K$.

Curve 3 in FIG. 2a shows the measured brightness values, each of which was determined for a respective measuring point $X_I$ on the X-axis without taking the preceding measured values $N_1$ and the following measured values $N_2$ into consideration. The graph shows a very strongly fluctuating curve from which no reliable data concerning the surface structure can be derived. Curve 3 thus shows the result of the brightness measurement without the process according to the invention.

Curve 4 shows the result of the measurement process according to the invention. An elongated wave, which can be accurately analyzed with respect to its amplitude and its wavelength, is clearly visible here. It is thereby possible to distinguish between short-wave and long-wave surface disturbances in a painted surface. Short-wave surface disturbances in a painting are, for example, caused by spray mists, while long-wave structures are conditioned by flow disturbances in the paint. It is thus possible by means of the analysis to determine that a certain percentage of painted surfaces exhibit long-wave disturbances, i.e., flow disturbances, and to improve the painting process accordingly.

Since, as shown in FIG. 2a, a series of measured values must be recorded following and preceding a certain measuring point on the surface, it has proven to be particularly favorable that all measured brightness values are determined first and entered in a data base, and that the measured values are then subsequently read from the memory and evaluated in the manner described.

For the evaluation of painting of automobile bodies, it has proven to be particularly favorable to select a length of 11 cm as the measurement length, from which 1300 measured values are recorded. These measured values are stored and then analyzed.

In an improvement of this method, the numbers $N_1$ and $N_2$ of the measured values used for deriving a measured surface value at a location $X_K$ can then be varied. If the number is lower, e.g., 10 measured values to the left and right of $X_K$, the short-wave disturbances are much more prominent; if the number is greater, the long-wave disturbances become more clearly visible.

Figure 2B:
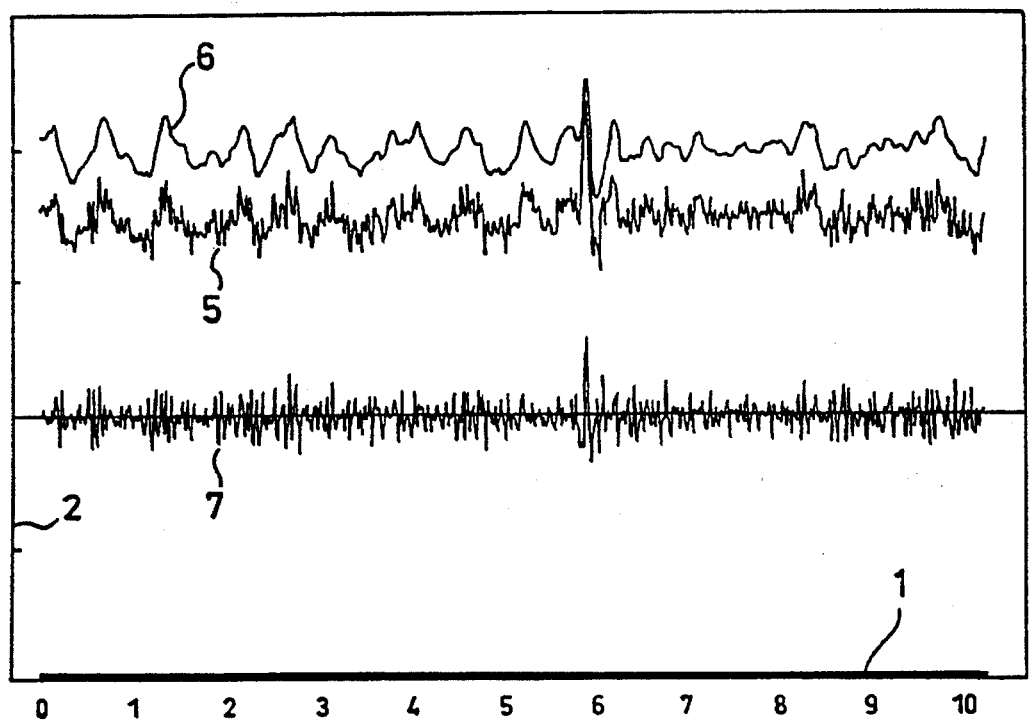
FIG. 2b is a result obtained using a process according to the invention.

FIG. 2b shows by means of actual recorded measured values how this different analysis influences the measurement result. The X-axis, which is again designated 1, indicates the location of each measuring point on the surface being measured while the numbers 0 to 10 represent the straight-line distance in centimeters. The total measured distance is thus here about 11 cm.

The respective measurement results, with dimensionless values, are plotted on the Y-axis which is indicated as 2.

Curve 5 indicates the measured brightness values which were actually recorded during the measurement. These were stored in a memory and were then subsequently analyzed in a process according to the invention. Curve 6 shows the measured surface values which are obtained from the long-wave analysis of the measured brightness values. It can be clearly seen that this yields a basic surface structure which is free of smaller variations and from which, e.g., the flow of the paint can be evaluated.

Curve 7 shows the measured surface values for a short-wave analysis of the measured brightness values depicted in curve 5. The long-wave surface disturbances do not play any role here, as can be seen.

One or several quality indices for the evaluation of the surface quality are now obtained from curves 6 and 7. This can be carried out, e.g., by determining the variance of the measured surface values.

The schematically drawn device in FIG. 1 functions according to the previously described principle; i.e., it records at once a predetermined number of measuring points with a constant distance and then evaluates this according to the process according to the invention.

The measuring device has a laser 10 which preferably functions in the wavelength range of visible light, which improves the measurement and is also more favorable with respect to safety. The light which is emitted from the laser at an angle of 60° to the surface is reflected from the surface and strikes a photodetector 12. The photodetector 12 has a filter which is adjusted to the wavelength of the laser so that the ambient light exerts only a negligibly low influence.

The device also has a position pickup 14 which determines the displacement intervals of the device in relation to the surface being measured and produces a pulse when a certain distance has been covered and a new measured value can be recorded.

The laser 10, the photodetector 12, and the position pickup 14 are connected via respective signal processors 18, 19, and 20 to a processor, preferably a microprocessor 25, which regulates the function of the entire device. The microprocessor is in turn connected to a timer 27, a standard value memory 28, and a memory for optional access 29. The timer functions to regulate the time for the entire device; a program that controls the device is stored in the standard value memory 28. The measurement data are stored in the memory 29.

The microprocessor 25 is, in turn, connected through a signal processor 32 to a display 34 which functions to indicate the measured values and for dialogue with the user. In addition, an LED 36, which for safety reasons always lights up when the laser is active, is connected to this signal processor.

A switching device 38, which has several switches so that control signals can be given by the user, is also included.

A battery (not represented in FIG. 1) is used to supply power to the device.

The function of this device is as follows.

The device is moved, either as a unit or only with a component which contains the laser 10, the photodetector 12, and the position pickup 14, relative to the surface being tested 8. In this step the speed of this movement does not play any role. The laser is supplied with energy and beams light onto the reflecting surface. The reflected light is recorded by the photodetector and conducted over the signal processor circuit 19, where, e.g., an A/D conversion takes place, to the microprocessor 25. A first measured value is recorded and stored in the memory 29 whereby the position pickup 14 determines the position of this first measuring point. Subsequently, a new measured value is determined and read when the position pickup produces a signal indicating that the respective measuring point on the surface has advanced along the predetermined distance. The laser and the photodetector are thereby constantly in operation. As soon as, in the preceding case, a measured distance of 11 cm has been covered, and thus about 1300 measured values have been stored in the memory 29, the actual measuring process is completed.

The device can thus be set up so that the measured surface values and one or several quality indices, which provide the user with information about the quality of the tested surface, are determined from these values by means of the program stored in the memory 28 and shown on the display 34.

In an alternative configuration of the device, the values can also be read out to an external computer which then determines the measured surface values and the quality indices from the measured values. In the latter version, the memory 29 and the program 28 are set up so that several series of measured values, e.g., 5 or 10 for different tested surface sections, can be recorded in the memory 29.

It is, of course, also possible to connect the device on-line to a computer, i.e., to first collect the measured values and then transfer them in one reading process to the controlling computer. The results determined by the controlling computer can thereby be transferred back to the device and displayed there.

Figure 3:
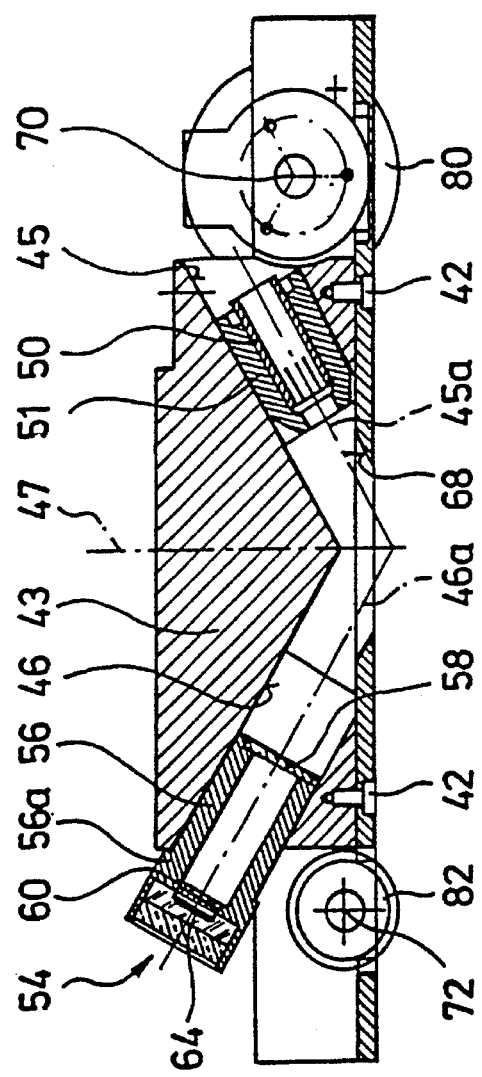
FIG. 3 is a schematic longitudinal section of an embodiment of a device according to the invention.

One embodiment of a device which is designed according to the block schematic in FIG. 1 will now be described with reference to FIGS. 3 and 4.

The device represented is designed so that it can be set up in a housing whose dimensions are smaller than 180 mm×50 mm×120 mm. However, the device is only partially represented in FIGS. 3 and 4.

The device has a U-shaped frame 40 which is constructed, e.g., of aluminum, and which extends essentially over the entire length of the device. The frame has a bottom plate 40a, a first side flange 40b, and a second side flange 40c. The frame has a symmetry plane 41 which is perpendicular to the bottom plate 40a.

A block 43 is screwed in place on the bottom plate 40a by means of screws 42. The block 43 has two cylindrical holes 45 and 46 whose axes 45a and 46a lie in the symmetry plane 41. The holes are both inclined by exactly 30° relative to the bottom plate 40a which means that they each have an angle of 60° to the vertical symmetry plane 41. The holes are set up so that their axes 45a and 46a intersect exactly at a point of the surface being measured.

A conventional semiconductor laser 50, which emits a light beam with a wavelength of 670 nm in a direction which exactly corresponds to the direction of the axis 45a, is set up in the first hole 45. The laser 50 is cemented into the hole 45 with a plastic block 51.

The photodetector 54 is set up in the hole 46. The detector contains a tube 56 which is closed on its front end by means of a color filter 58. The color filter is adjusted so that it essentially transmits only the wavelength of the laser light of the laser 50. An infrared filter 60, which is used as a thermal insulation filter as well as a rectangular diaphragm whose aperture is about 0.3×0.8 mm, is located on the end 56a of the tube. To this is connected the light-sensitive part 64 in which an electrical analog signal, which is a function of the amount of incidental light, is produced.

An aperture 68, which permits the exit and re-entry of the laser light from the device, is in the lower region of the bottom plate 40a. In order to permit working with the device outside of special light-protection areas and also without protective glasses, the power of the laser is adjusted so that it is a maximum of 1 mW.

This power is also preferably controlled by the microprocessor 25 in a suitable manner.

Two axles 70 and 72, which are set up in holes 73 of the side flanges 40b and 40c and penetrate the side flanges, are located in the end regions of the frame 40. The axles 70 and 72 are parallel to the bottom plate 40a of the frame 40.

Figure 4:
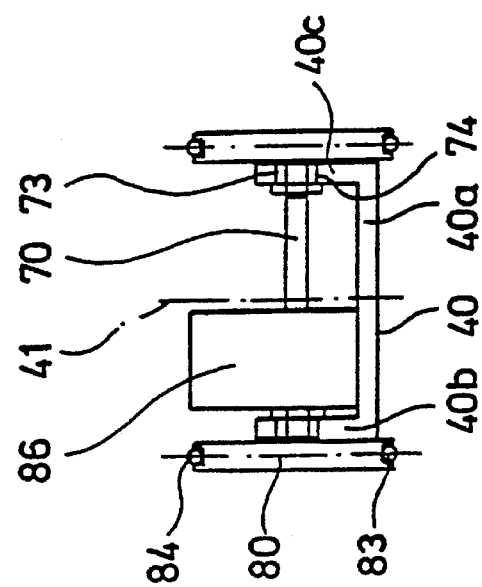
FIG. 4 is a front view of the embodiment of FIG. 3 taken at the right side of FIG. 3.

The guiding of the axles in the side flanges is carried out by means of bearing housings 74 which are indicated schematically in FIG. 4.

Primary wheels 80 with a larger diameter and secondary wheels 82 with a smaller diameter are impressed on both ends of the axles 70 and 72. The wheels are constructed of plastic and have a groove 83 along the perimeter into which a rubber ring 84, preferably an O-ring, is inlaid.

The Shore hardness of these rubber rings 84 is selected so that the ring is soft enough on the one hand to allow contact with the surface being measured without damaging the surface, but so that it on the other hand is not so soft that it allows dust particles and the like to settle on it.

The axle 70 of the large wheels 80 penetrates a conventional angle of rotation sensor 86 and is connected to it free of rotational play. The housing of the angle of rotation sensor 86 is fixed with reference to the frame 40. The angle of rotation sensor is adjusted so that an electrical pulse is always produced when the axle 70 rotates through a predetermined angle, e.g., 1°.

The frame 40 and the block 43 attached to it are attached in a housing which is not represented for the sake of clarity. This housing also contains a battery and all electronic components which were described above with reference to FIG. 1. The housing is set up so that the wheels 80 and 82 and their respective axles can rotate freely.

The function of this device is thus as follows.

The housing, which when installed has approximately the size of a thick paperback book, is held in the hand by an operator and placed on the surface being measured using the wheels 80 and 82. The device is then moved by hand corresponding to the orientation of the wheels 80 and 82 over the surface so that the wheels rotate. After the beginning of the measuring cycle, 1300 measuring points are recorded and stored in the memory 29, as described. The required equidistance of the measuring points is controlled by the angle of rotation sensor 86 whose pulses are used by the microprocessor for regulating the measurement recording.

The speed with which the device is moved over the surface being tested and whether the speed is changed while the measured values are recorded is, therefore, unimportant to measurement accuracy.

Based on the distance which the contact points of the wheels 80 and 82 on the surface of the profile 40 being measured exhibit, it is ensured that the device is suitable for scanning curved areas, e.g., in the fender or roof region of a vehicle body. In this context, it should be noted that vehicle bodies never have completely planar surfaces due to technical reasons of manufacture.

In order to ensure a reliable measurement recording under all conditions, the microprocessor can also control whether all required marginal conditions of the measurement have been maintained. It can then, e.g., issue a warning if the measuring path along which the device was moved was too short and the like.

The device according to the invention, as it has been described above, offers considerable advantages for routine testing, e.g., in vehicle painting. For instance, the device according to the invention can be placed on the paint locations where the tester suspects or determines deficiencies in quality from a visual inspection, and the quality index or indices of the surface can be determined. The tester can then determine whether the tested paint area is still within the permissible tolerance margins for paint quality by means of an exactly defined value. He is thereby no longer dependent on his subjective feeling, in contrast to the conventional process.

In addition, the device can provide detailed information on the wave region in which the respective optical disturbance is located so that the analysis of the apparent disturbances can be used for optimizing the painting equipment.

In addition to the described manual use of the device, it is also possible to use the device automatically. As an example, a device, as depicted in FIGS. 3 and 4, can also be placed by a handling robot on a surface being tested. In this case, the device is then preferably connected on-line to the computer which influences the control of the manufacturing process.

In case corresponding equipment is available, the wheels and the angle of rotation indicator can also be omitted, if necessary, during an automatic measurement recording, and a different technique can be used for recording position.

I claim:

1. A process for quantitative measurement of the appearance of a reflective surface comprising:

measuring light reflected from each of $X_i$ locations on a reflective surface, where i ranges from 1 to n, the locations being uniformly spaced along a path on the reflective surface, thereby determining a brightness value for each of the locations $X_i$;

storing the brightness values for each of the locations $X_i$;

for a location $X_K$ on the path, retrieving the brightness values for $N_1$ locations on the path immediately before the location $X_K$, retrieving the brightness values for $N_2$ locations on the path immediately after the location $X_K$, and retrieving the brightness value for the location $X_K$, where $N_1$ and $N_2$ are integers;

determining a surface value for the location $X_K$ by statistically analyzing the brightness values of the $N_1$ locations, the $X_K$ location, and the $N_2$ locations; and repeating the steps of retrieving brightness values and determining surface values for each of a plurality of points $X_i$ and plotting the surface values to produce a quality characteristic of the reflective surface.

2. The process of claim 1 wherein $N_1$ equals $N_2$.

3. The process of claim 1 wherein the statistical analysis comprises calculating the surface value for the point $X_K$ as a mean of the brightness values of the $N_1$ locations, the $N_K$ location, and the $N_2$ locations.

4. A process for quantitative measurement of the appearance of a reflective surface comprising:

measuring light reflected from each of $X_i$ locations on a reflective surface, where i ranges from 1 to n, the locations being uniformly spaced along a path on the reflective surface, thereby determining a brightness value for each of the locations $X_i$;

storing the brightness values for each of the locations $X_i$;

for a location $X_K$ on the path, retrieving the brightness values for $N_1$ locations on the path immediately before the location $X_K$, retrieving the brightness values for $N_1$ locations on the path immediately after the location $X_K$, and retrieving the brightness value for the location $X_K$, where $N_1$ is an integer;

determining a first surface value for the location $X_K$ by statistically analyzing the brightness values of the $N_1$ locations and the $X_K$ location;

repeating the two preceding steps of retrieving brightness values and determining first surface values for each of a plurality of points $X_i$ and plotting the first surface values to produce a first quality characteristic of the reflective surface;

for a location $X_K$ on the path, retrieving the brightness values for $N_2$ locations on the path immediately before the location $X_K$, retrieving the brightness values for $N_2$ locations on the path immediately after the location $X_K$, and retrieving the brightness value for the location $X_K$, where $N_2$ is an integer and $N_2$ does not equal $N_1$;

determining a second surface value for the location $X_K$ by statistically analyzing the brightness values of the $N_2$ locations and the $X_K$ location; and repeating the immediately two preceding steps of retrieving brightness values and determining second surface values for each of a plurality of points $X_i$ and plotting the second surface values to produce a second quality characteristic of the reflective surface.

5. The process of claim 4 wherein the statistical analyses comprise calculating the first surface value for the point $X_K$ for the first quality characteristic as a mean of the brightness values for the $N_1$ locations and the $N_K$ location and calculating the second surface value for the point $X_K$ for the second quality characteristic as a mean of the brightness values for the $N_2$ locations and the $N_K$ location.

6. A portable device for quantitative measurement of the appearance of a reflective surface comprising:

a frame;

a light source mounted on the frame for producing a light beam and directing the light beam at a reflective surface;

a photodetector mounted on the frame for detecting reflected light of the light beam reflected from the reflective surface and producing an electrical signal having a magnitude indicating intensity of the reflected light, thereby indicating brightness of the reflective surface, the light source and photodetector having a fixed geometrical relationship with respect to each other;

wheels rotatably mounted on the frame for contacting a reflective surface, rotating upon movement of the frame along a path on the reflective surface, maintaining the frame in a fixed relationship to the reflective surface;

a relative position indicator connected to the measuring wheel for generating an electrical pulse each time the measuring wheel rotates through a fixed angular increment;

control means connected to the photodetector and the relative position indicator for successively measuring the intensity of the electrical signal for each of a plurality of uniformly spaced measuring locations on the reflective surface in response to electrical pulses produced by the relative position indicator, the pulses indicating relative locations along the path; and a memory connected to the control means for storing the magnitudes of the electrical signals produced by the photodetector for each of the measuring locations and relative location information based upon the electrical pulses produced by the relative position indicator.

7. The device of claim 6 wherein the light source is a semiconductor laser.

8. The device of claim 7 comprising a color filter mounted on the frame adjacent the photodetector for transmitting light of a wavelength produced by the laser.

9. The device of claim 7 wherein the laser produces visible light.

10. The device of claim 6 wherein, when the measuring wheel contacts the reflective surface, the light source is separated from the reflective surface by a distance of less than twelve centimeters.

* * * * *

UNITED STATES PATENT AND TRADEMARK OFFICE
CERTIFICATE OF CORRECTION

PATENT NO. : 5,596,412
DATED : January 21, 1997
INVENTOR(S) : Lex

It is certified that error appears in the above-indentified patent and that said Letters Patent is hereby corrected as shown below:

On the title page:
Item 73: Assignee, change "BYK-GARDNER" to --BYK-GARDNER, GmbH--.

Signed and Sealed this

Seventeenth Day of June, 1997

Attest:

BRUCE LEHMAN

Attesting Officer

Commissioner of Patents and Trademarks